United States Patent
Butler et al.

(10) Patent No.: US 10,117,629 B2
(45) Date of Patent: Nov. 6, 2018

(54) HIGH ENERGY GRATING TECHNIQUES

(71) Applicant: Board of Supervisors of Louisiana State University and Agricultural and Mechanical College, Baton Rouge, LA (US)

(72) Inventors: Leslie G. Butler, Baton Rouge, LA (US); Kyungmin Ham, Baton Rouge, LA (US); Warren W. Johnson, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 342 days.

(21) Appl. No.: 14/958,882

(22) Filed: Dec. 3, 2015

(65) Prior Publication Data
US 2016/0161427 A1    Jun. 9, 2016

Related U.S. Application Data

(60) Provisional application No. 62/087,230, filed on Dec. 3, 2014.

(51) Int. Cl.
*A61B 6/00* (2006.01)
*G01N 23/20* (2018.01)
(Continued)

(52) U.S. Cl.
CPC .............. *A61B 6/484* (2013.01); *A61B 6/032* (2013.01); *A61B 6/4291* (2013.01); *G01N 23/04* (2013.01);
(Continued)

(58) Field of Classification Search
CPC ...................................................... A61B 6/484
(Continued)

(56) References Cited

U.S. PATENT DOCUMENTS

| | | |
|---|---|---|
| 5,812,629 A | 9/1998 | Clauser |
| 7,983,381 B2 | 7/2011 | David et al. |

(Continued)

FOREIGN PATENT DOCUMENTS

EP    1731099 A1    12/2006

OTHER PUBLICATIONS

Mathews, Jon, Walker, Robert Lee, Mathematical methods of physics, 1964, pp. 360-369, W.A. Benjamin Inc.
(Continued)

*Primary Examiner* — David P Porta
*Assistant Examiner* — Abra Fein
(74) *Attorney, Agent, or Firm* — John B. Edel; Edel Patents LLC

(57) ABSTRACT

Imaging techniques that may be used in applications such as differential phase contrast imaging are disclosed that include, for example, configuring a beam source and a beam detector such that a beam connects the two, positioning an object, a phase grating and an analyzer grating in the beam path, producing multiple data sets based on various analyzer grating positions, and conducting a regression analysis using a predetermined function having a set of fitting coefficients to establish those fitting coefficients. In those techniques, the fitting coefficients may be used to characterize a set of interference properties associated with the object.

20 Claims, 11 Drawing Sheets

(51) Int. Cl.
    *G01N 23/04* (2018.01)
    *A61B 6/03* (2006.01)
(52) U.S. Cl.
    CPC . *G01N 23/20075* (2013.01); *G01N 2223/401* (2013.01)
(58) Field of Classification Search
    USPC ........................................ 250/390.02; 378/36
    See application file for complete search history.

(56) References Cited

U.S. PATENT DOCUMENTS

| | | | | |
|---|---|---|---|---|
| 7,924,973 | B2 | 11/2011 | Kotler et al. | |
| 8,767,047 | B2* | 7/2014 | Molnar | G06T 1/0007 348/43 |
| 8,855,265 | B2* | 10/2014 | Engel | A61B 6/00 378/36 |
| 9,767,982 | B2* | 9/2017 | Behling | H01J 35/08 |
| 2003/0186142 | A1* | 10/2003 | Deshmukh | G02B 6/02085 430/30 |
| 2007/0183582 | A1 | 1/2007 | Baumann et al. | |
| 2007/0183563 | A1* | 8/2007 | Baumann | A61B 6/032 378/19 |
| 2009/0316857 | A1 | 12/2009 | David et al. | |
| 2010/0290590 | A1 | 11/2010 | Ouchi et al. | |
| 2011/0051889 | A1* | 3/2011 | Sato | B26D 3/06 378/36 |
| 2012/0057677 | A1 | 3/2012 | Vogtmeier et al. | |
| 2013/0308751 | A1* | 11/2013 | Koehler | G21K 1/06 378/36 |
| 2016/0254069 | A1* | 9/2016 | Preusche | G21K 1/06 378/149 |

OTHER PUBLICATIONS

Weitkamp, David et al. Hard X-ray phase imaging and tomography using a grating interferometer, Spectrochimica Acta Part B 62 (2007) 626-630.

Schulz, Joachim, Gratings for X-Ray Differential Phase-Contrast-Imaging, http://www.micro-works.de/t3/fileadmin/pdf/microworks_gratings_for_DPCI_overview.pdf, 2012.

* cited by examiner

| Grating steps | Algorithm[a] | Transmission | ΔDPC | Error[b] (%) | Dark-field | $\chi_\nu^2(sample)$ |
|---|---|---|---|---|---|---|
| 1-10 | LM, FT, Basis | 0.9345 | −0.1743 | ... | 1.0819 | 0.63 |
| 1-6, 8-10 | LM | 0.9331 | −0.1641 | 5.88 | 1.0904 | 0.75 |
| 1-6, 8-10 | Basis | 0.9331 | −0.1641 | 5.88 | 1.0904 | 0.75 |
| 1-6, 8-10 | FT | 0.9233 | −0.1457 | 16.4 | 1.1530 | 5.42 |
| 1-16 | Basis | 0.9376 | −0.1862 | 6.83 | 1.0985 | 1.34 |
| 2-11 | Basis | 0.9353 | −0.1765 | 1.24 | 1.0612 | 0.17 |

[a]LM: Levenberg-Marquardt, FT: discrete Fourier transform, and Basis: new algorithm in Example 1.
[b]Error with respect to Levenberg-Marquardt fit for grating steps 1-10.

Fig. 6

HIGH ENERGY GRATING TECHNIQUES

This application claims the benefit of provisional application No. 62/087,230 filed on Dec. 3, 2014 and entitled X-Ray Grating Interferometry.

This invention was made with government support under Contract No. CHE-0910937 awarded by the National Science Foundation. The government has certain rights in this invention.

High energy grating techniques described herein may be used in imaging and other applications dealing with large data sets. Certain high energy grating techniques disclosed herein may be particularly useful in the processing of data associated with differential phase contrast imaging data sets.

BRIEF DESCRIPTION OF THE DRAWINGS

FIG. 6 is a table comparing the results of using three methods to analyze data for a single pixel.

DETAILED DESCRIPTION

Figure 1:
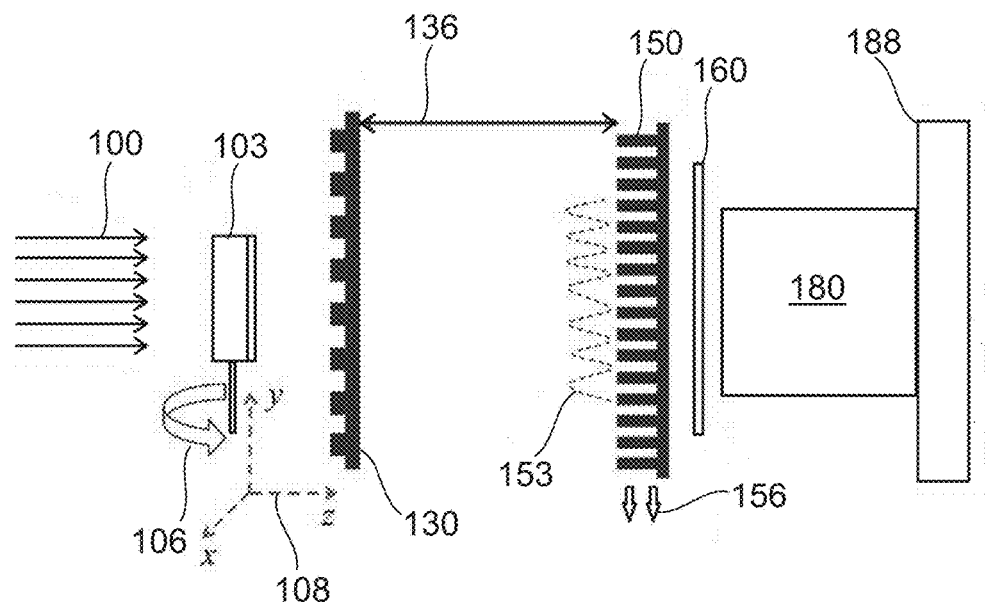
FIG. 1 shows an experimental setup associated with Examples 1-3.

Techniques described herein aid in the efficient handling of large data sets generated by grating-based X-ray and neutron interferometry tomography using phase-stepping methods. The methods described solve for the parameters to calculate transmissions, differential phase contrast, and dark-field images. The methods take advantage of the vectorization inherent in high-level languages found in mathematical and symbolic computing programs such as Mathematica (Wolfram Research of Champaign, Ill.) and MATLAB (The MathWorks, Inc., Natick, Mass.) and can solve a 16×1 k×1 k data set in less than a second. In addition, the methods can function with partial data sets which was demonstrated by the processing of a 16-step grating data set with partial use of the original data chosen without any restriction.

Grating-based interferometry methods disclosed herein may be used for X-ray and neutron imaging beamlines to perform phase contrast imaging and tomography. Applications for these methods may be found in materials science, biomedical science, and beam wavefront and optics characterization.

Techniques described herein may outperform conventional techniques for the handling of the large data sets associated with various interferometry techniques. In particular, the methods described herein may be superior to a discrete Fourier transform algorithm, which is quite popular, because of significant differences in accuracy. For example, a discrete Fourier transform algorithm may suffer from spectral leakage when the grating steps are not uniformly spaced within a period. Further, a Levenberg-Marquardt algorithm is capable of solving non-uniformly spaced data, but may suffer from high calculation times as compared to the methods described herein.

Example 1

A grating-based phase-stepping interferometry data set consists of a set of pixelated images acquired as a function of a grating stepping. The triangular interferometric signal is approximated as a sinusoid for which and the method seeks to determine the amplitude and phase. The sinusoid period is usually known from the grating motion. The speed of this method is based on pre-computation of the sinusoidal functions and vectorization of the pixel data. The amplitude and phase may be calculated with standard matrix manipulations.

The interferometry data are a set of X-ray counts $c_{gp}$, where $g=1, \ldots, M$ is the index that identifies the exposure, with one exposure at each grating displacement $x_g$; and $p=1, \ldots, N$ is the index that identifies the pth pixel. Typically M~7 to 16 and N~millions. The adapted fitting equations below transform the fitting operation into a simple matrix problem. Each set of exposures is fit pixel by pixel, $c_{gp}$, to each pixel's expected dependence on grating position $x_g$:

$$\hat{c}_{gp} = a_{1p} + a_p \sin\left(\frac{2\pi}{p_{grat}} x_g + \phi_p\right) \qquad (1)$$

$$\equiv [1] a_{1p} + \left[\sin\left(\frac{2\pi}{p_{grat}} x_g\right)\right] a_p \cos(\phi_p)$$

$$+ \left[\cos\left(\frac{2\pi}{p_{grat}} x_g\right)\right] a_p \sin(\phi_p) \qquad (2)$$

-continued $$\equiv \sum_{\mu=1}^{3} B_{g\mu} a_{\mu p} \quad (3)$$

$$a_{2p} \equiv a_p \cos(\phi_p), \ a_{3p} \equiv a_p \sin(\phi_p), \quad (4)$$

where $a_p$ and $\varphi_p$ are the amplitude and phase of the interference term for the pth pixel, and $p_{grat}$ is the period of the translated grating. The interference term is expressed in both polar form, as shown in Eq. (1) and Cartesian form, as shown in Eq. (4). The latter is used to define the M×3 matrix B, Eq. (3), that represents the three fitting functions shown in brackets in Eq. (2): constant, sine, and cosine. The $a_{\mu p}$ is one element in the coefficient matrix a, which is a 3×N matrix of amplitudes, or weights, of the three fitting functions for the N pixels. a will later be reshaped into a 3D matrix with dimensionality [rows, columns, 3]. The best fit can be chosen to be the set of coefficients $a_{\mu p}$ that minimize the deviation-squared, $D_p$, for each pixel, defined by $$D_p \equiv \sum_{g=1}^{M} (c_{gp} - \hat{c}_{gp})^2. \quad (5)$$

To minimize $D_p$, the derivatives of each deviation-squared are calculated with respect to each component of a, set all deviations to zero, and solve the resulting matrix equations. The closed form expression for the coefficient matrix a is found to be $$a = G \cdot c, \quad (6)$$

where $$G = (B^T \cdot B)^{-1} \cdot B^T, \quad (7)$$

and where the superscript T indicates the matrix transpose. So the optimization problem is reduced to multiplying a 3×M fixed matrix G into the M×N data matrix c, to find the 3×N coefficient matrix a. With an efficient matrix manipulation program like MATLAB, the multiplication is extremely fast, of the order of 1 s for 1 k×1 k images times 16 grating steps. By inspection, the polar coefficients may be recovered from the Cartesian in the usual way:

$$a_p = \sqrt{a_{2p}^2 + a_{3p}^2}, \ \phi_p = \tan^{-1}(a_{3p}/a_{2p}). \quad (8)$$

The analysis was extented to use knowledge of the expected uncertainty or variance of each datum $\sigma^2_{gp}$ at the price of increased computing time. The model equation, Eq. (4), can be extended to include anharmonic terms to describe the grating effects more accurately and to include more sophisticated grating motion trajectories. More details about the derivation of Eq. (7) appear in a later section.

In the stepped-grating interferometry experiment, two data sets were measured. A reference data set was measured without the sample in the beam and a sample data set was measured with the sample in the beam:

$$\text{transmission} = \frac{a_{1p}(\text{sample})}{a_{1p}(\text{reference})}, \quad (9)$$

$$\text{differential phase contrast} = \phi_p(\text{sample}) - \phi_p(\text{reference}), \quad (10)$$

$$\text{dark-field} = \frac{a_p(\text{sample})/a_p(\text{reference})}{a_{1p}(\text{sample})/a_{1p}(\text{reference})}, \quad (11)$$

where the polar coefficients are defined in Eq. (1).

Example 2

Test Configuration

The X-ray interferometry data were collected with a prototype experimental setup at the Advanced Photon Source and Center for Nanoscale Materials, Office of Science User Facilities configured as a two-grating interferometer at the 2-BM-B beamline arranged as depicted in FIG. 1. The stepped-grating system was installed 23 m downstream of the double multilayer monochromator, which provides a monochromatic beam at 25 keV with 1% bandwidth. Phase grating 130, was optimized for π-phase shift at 25 keV with a period of 4.8 μm; Analyzer grating 150, had a period of 2.4 μm. The gratings were produced by Microworks (Karlsruhe, Germany) and to support the high-aspect ratio structures, both gratings included support structures: the Phase grating 130 was fabricated with a broken-line structure and the Analyzer grating 150 included a bridge-structure connecting adjacent lines.

Experiments were performed with Sample-to-phase grating distance 136 being 270 mm; a much shorter distance was desired but not possible due to mechanical interference between stacks of positioning stages in the test setup. Analyzer grating 150 was then positioned at the first fractional Talbot distance (m=1) 58 mm from Phase grating 130. Both phase and analyzer gratings were mounted on dual-tilt stages. Due to a smaller source size along the vertical plane, the X-ray radiation has its greatest coherence along the lab vertical; both gratings were positioned with the gratings aligned with the lab horizontal. The tomography sample rotation was about the lab vertical axis. The stepping scan motion along the lab vertical axis was performed with a piezoelectric-based positioner stage with a 200-μm range and sub-nanometer resolution. A 100-μm thick LuAG:Ce scintillator was imaged with a 10× optical magnification lens and a Coolsnap HQ2 CCD with a 1040×1392 array of 6.45-μm-square pixels; the small effective pixel size of 0.645 μm was used to accommodate another experiment performed in the test setup. The exposure time for each interferogram was 600 ms, and 16 interferograms were measured across 4/3 period of the analyzer grating structure. Reference data were collected before and after the tomography data; 601 projections were acquired in the angle range of 0° to 180°. Also, background images (X-rays off) were collected to account for CCD dark-current and the offset signal.

The tomography data were acquired over several hours. A comparison of the two reference data sets shows some drift as seen in the values of $\varphi_p$(reference). Test regions in the air around the tomography sample were used to correct the $\varphi_p$(reference) values as used in Eq. (10) and this correction was successful over about 40% of the field of view.

Tests associated with the present example were conducted on an experimental setup such as the setup depicted in FIG. 1 of the drawings. As depicted in FIG. 1, an X-ray beam 100 passed through Sample 103 which may be rotated around the Y axis of Axis set 108 in the direction indicated by Rotational arrow 106. The grating arrangement included a Phase grating 130 and an Analyzer grating 150. Phase grating 130 and Analyzer grating 150 were separated by a Sample-to-phase grating distance 136. Wave pattern 153 represents wave characteristics associated with fringe distortions entering Analyzer grating 150. Stepping direction 156 represents the direction of phase stepping of Analyzer grating 150. Scintillator 160 and Lens 180 were located in front of Charge-coupled device 188.

Figure 2A:
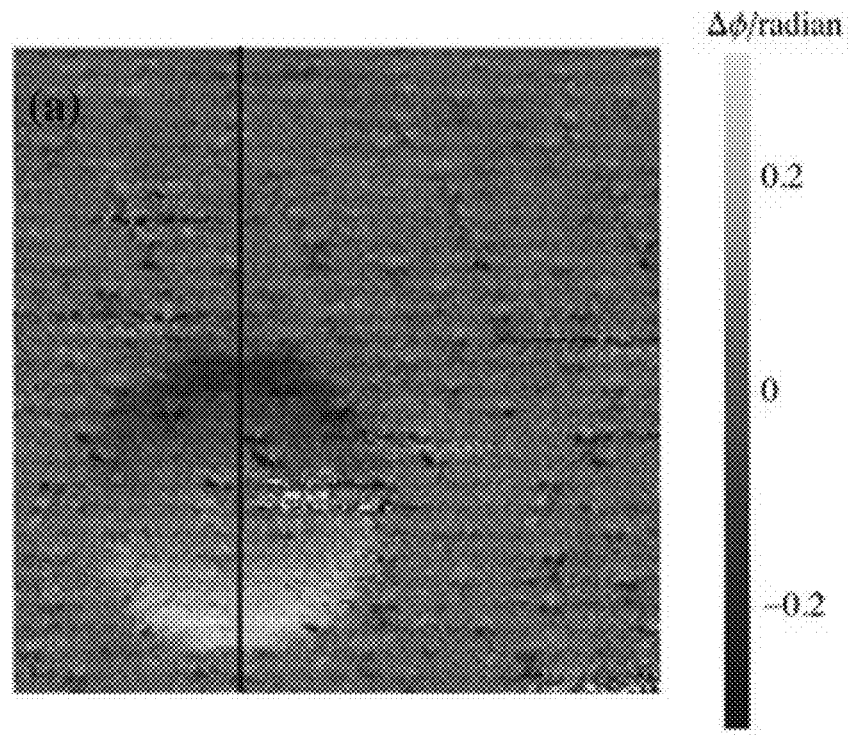
FIG. 2A is a differential phase contrast image based on Equation 10.
Figure 2B:
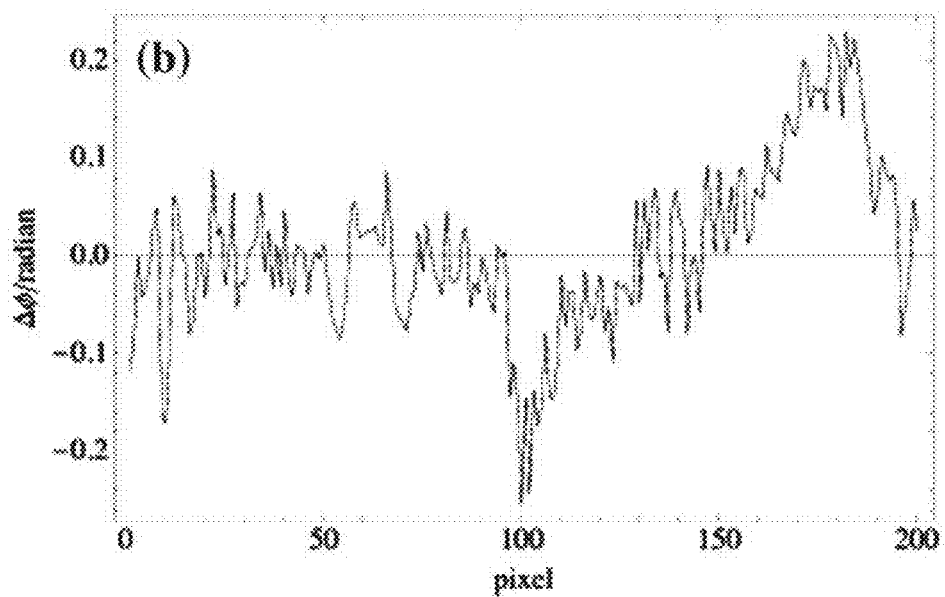
FIG. 2B contains the differential phase contrast line probe data.
Figure 2C:
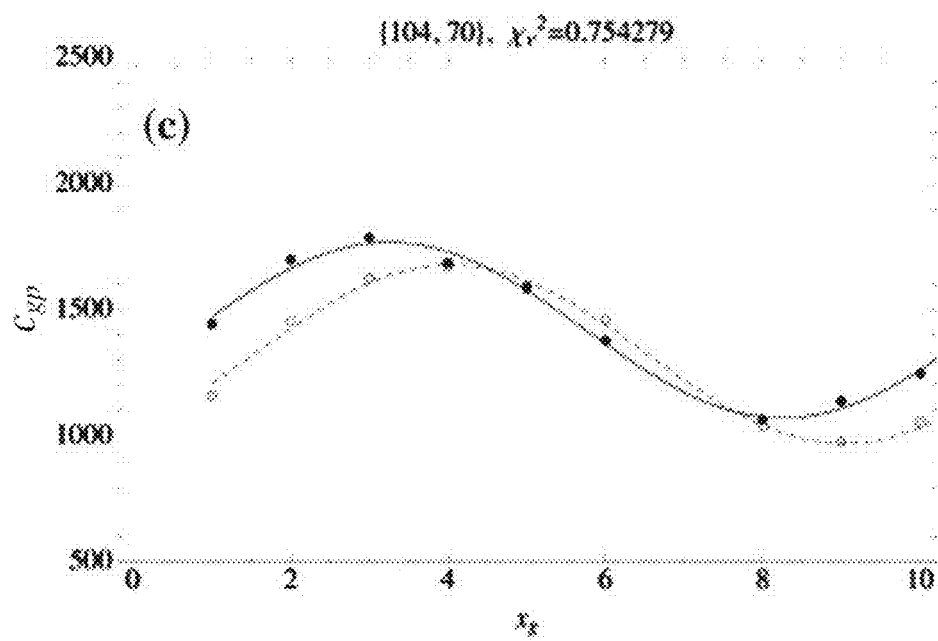
FIG. 2C depicts the reference interferometry data set and the interferometry data set for a particular pixel from FIG. 2E.
Figure 2D:
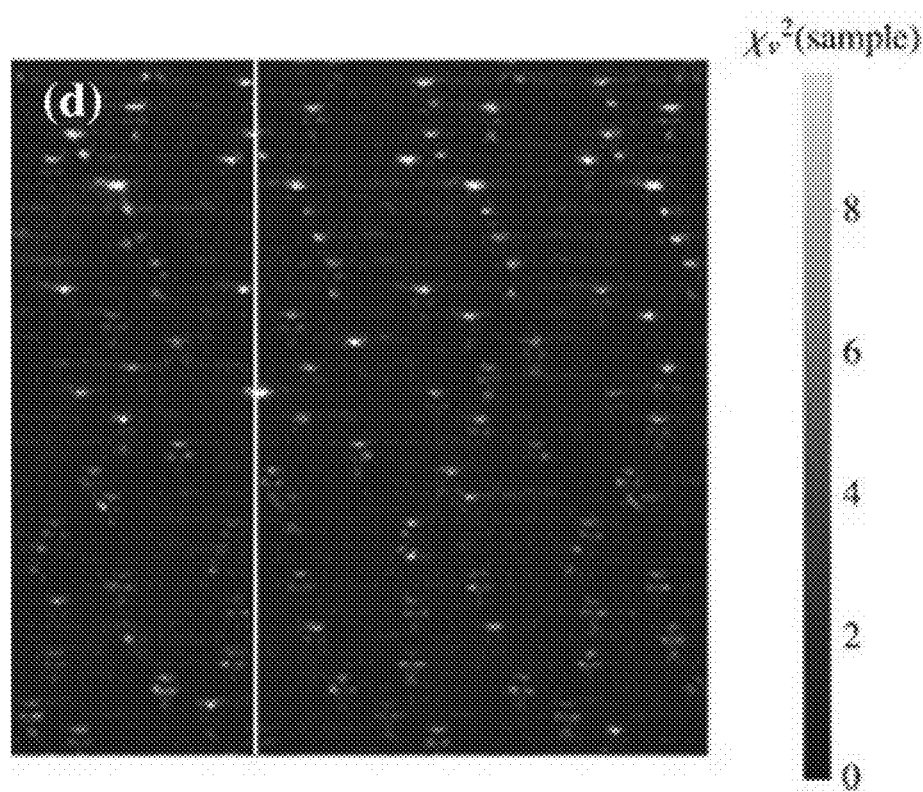
FIG. 2D is a plot of the reduced chi-square statistic for the sample.
Figure 2E:
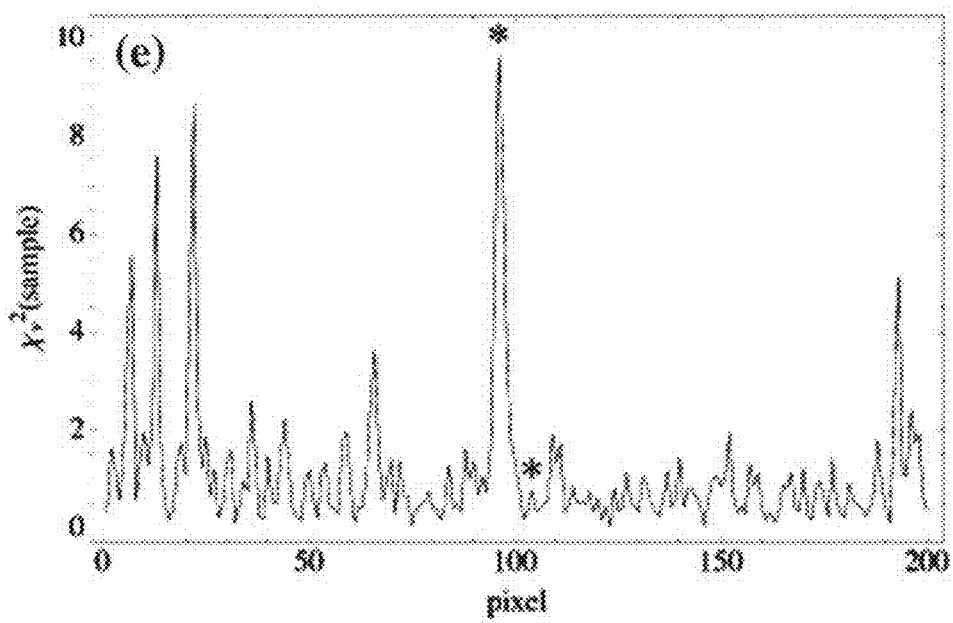
FIG. 2E shows a $\chi_\nu^2$ (sample) line probe plot.
Figure 2F:
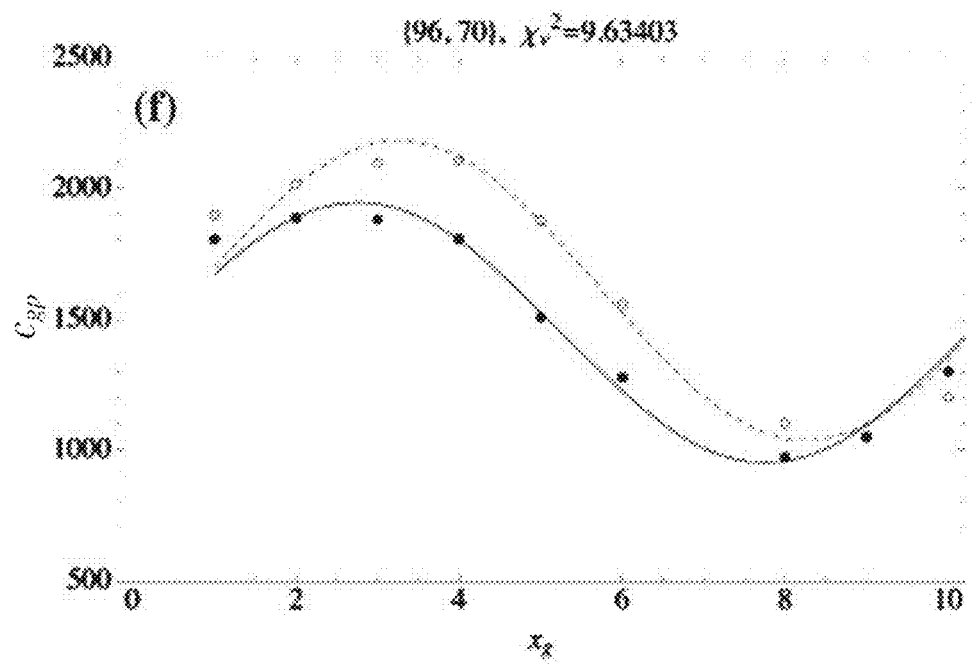
FIG. 2F depicts the reference interferometry data set and the interferometry data set for a particular pixel from FIG. 2E.

FIGS. 2A-2F of the drawings depict experimental and analytical results associated with testing and evaluations conducted based on the teachings described in Example 1 and Example 2. Data associated with FIGS. 2A-2F was gathered with a sample present and in the absence of the sample. The sample, as described in FIG. 1 as Sample 103, was a 50 µm diameter polystyrene sphere supported on a Polyimide film. As presented in FIGS. 2A-2F, the data from the seventh stepped grating position was omitted from the data processing that was conducted. The image origin was the upper left corner at {1,1} and the field of view is 200×200 pixels. FIG. 2A is a differential phase contrast image based on Equation 10 and FIG. 2D is a plot of the reduced chi-square statistic for the sample, $\chi_p^2$ (sample), based on Equation 1. FIG. 2B contains the differential phase contrast line probe data for column 70. FIG. 2E shows the $\chi_v^2$ (sample) line probe plot and indicates a wide range of values. Two representative pixels selected from FIG. 2E and indicated by asterisks on FIG. 2E are shown in FIGS. 2C and 2F. In FIGS. 2C and 2F the solid traces and closed circles indicate the reference interferometry data sets and the dashed traces and open circles indicate the interferometry data set with the sample in position. The poor fit depicted in FIG. 2F may be attributable to the grating support structures.

Figure 3A:
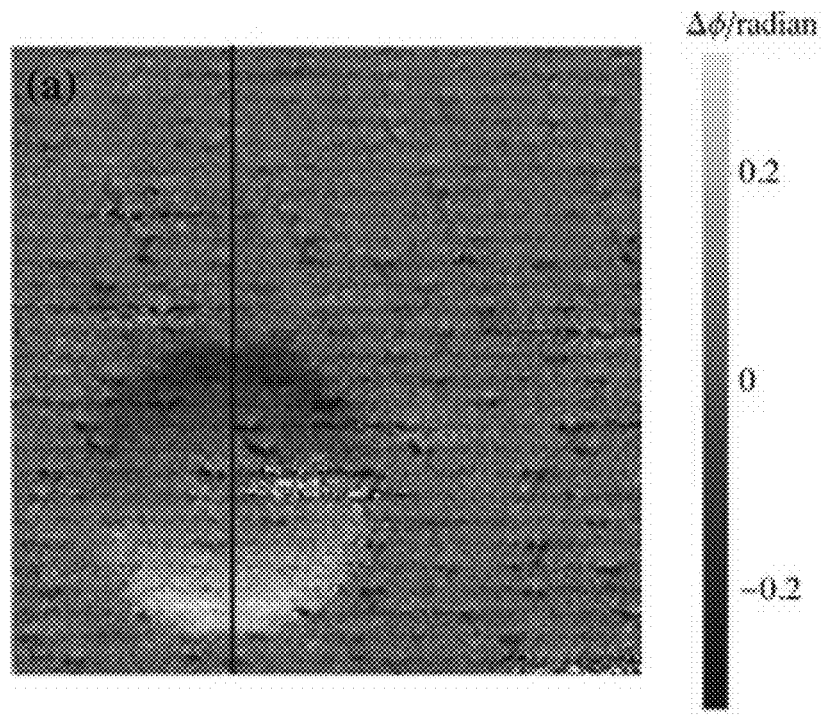
FIG. 3A is a differential phase contrast image based on a discrete Fourier transform method.
Figure 3B:
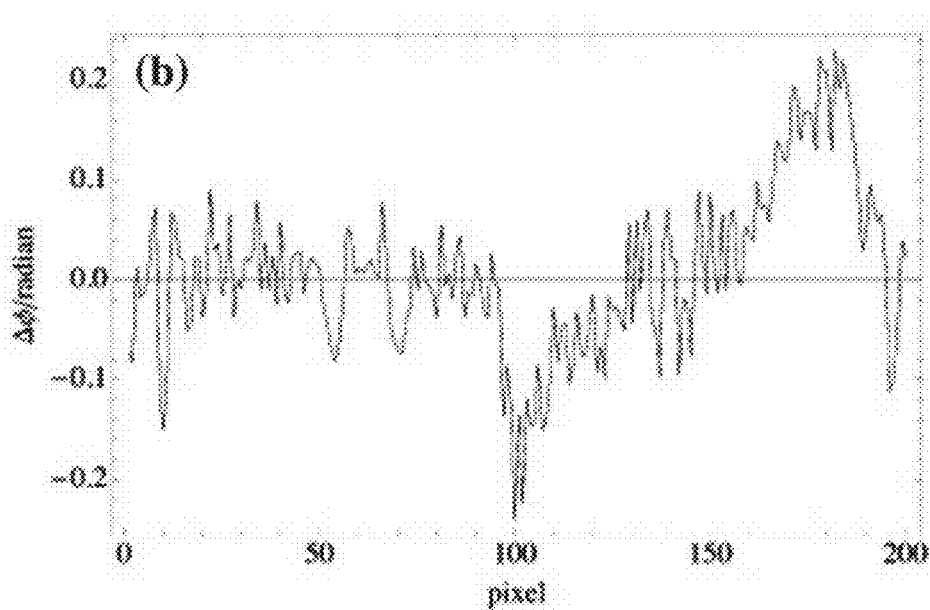
FIG. 3B contains the differential phase contrast line probe data for column 70.
Figure 3C:
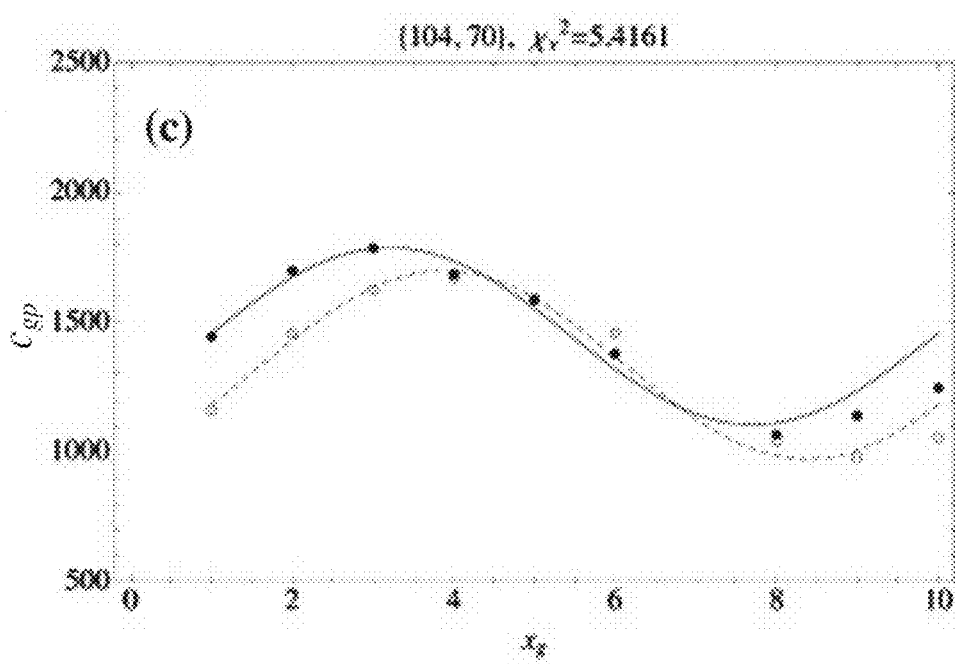
FIG. 3C depicts a reference interferometry data set and the interferometry data set for a particular pixel from FIG. 3E.
Figure 3D:
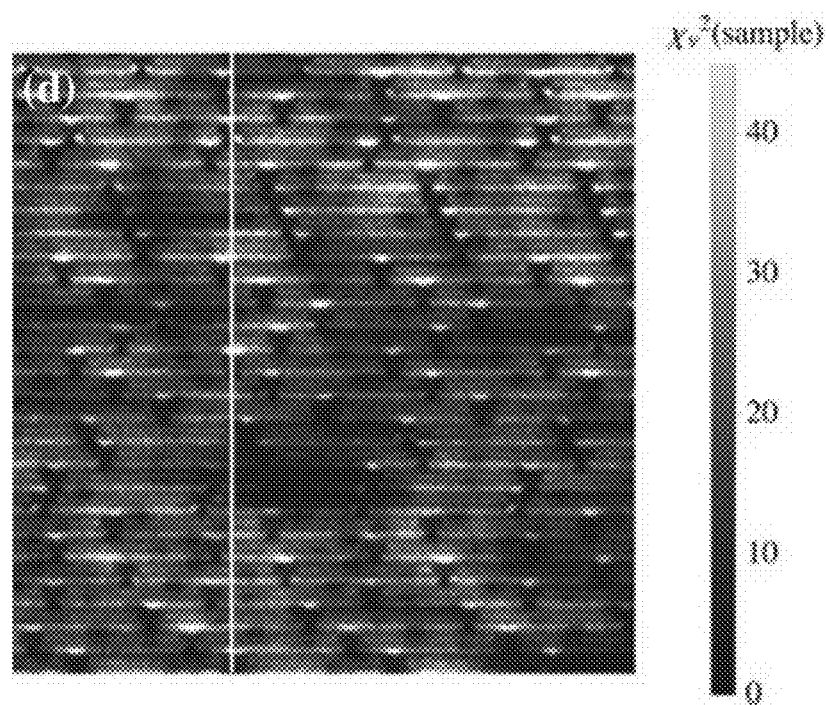
FIG. 3D is a plot of the reduced chi-square statistic for the sample.
Figure 3E:
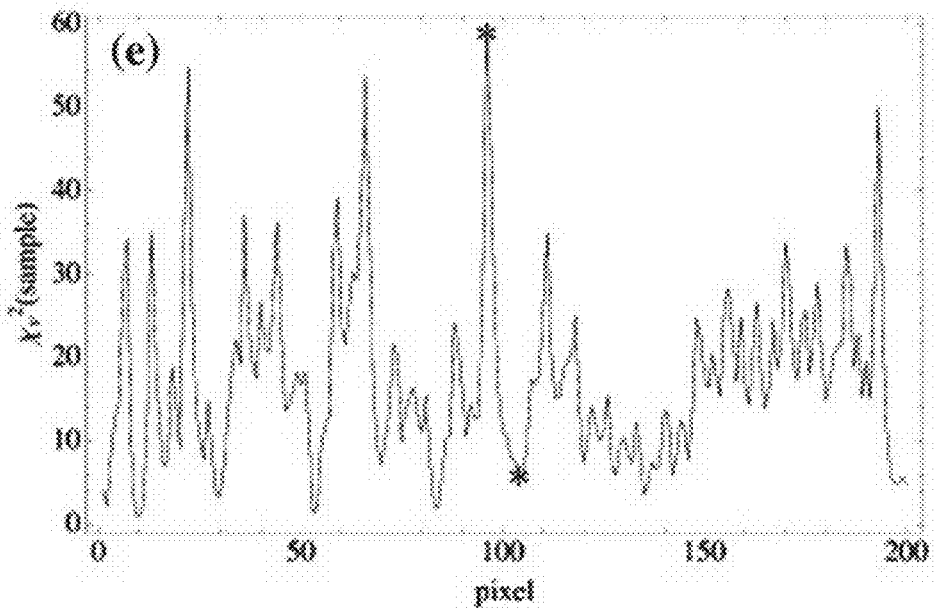
FIG. 3E shows a $\chi_\nu^2$ (sample) line probe plot.
Figure 3F:
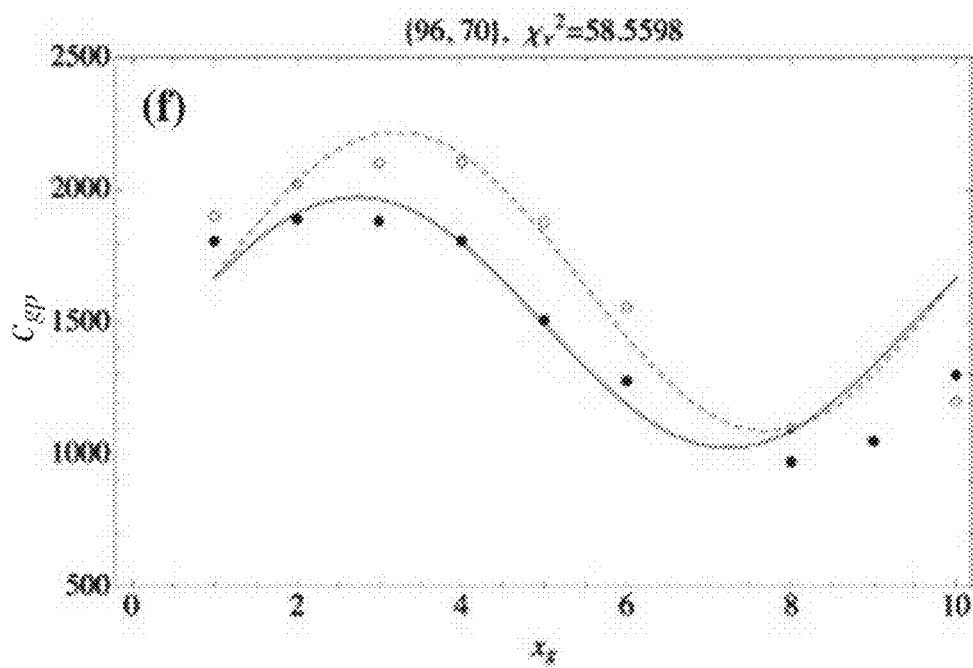
FIG. 3F depicts a reference interferometry data set and the interferometry data set for a particular pixel from FIG. 3E.

FIGS. 3A-3F of the drawings depict experimental and analytical results associated with testing and evaluations conducted based on discrete Fourier transform method is used to analyze the same data set as shown in FIGS. 2A-2F. As before, the data from the 7th grating step was eliminated from the processing. FIG. 3A is a differential phase contrast image. FIG. 3B contains the differential phase contrast line probe data for column 70. FIG. 3E shows the $\chi_v^2$ (sample) line probe plot. Two representative pixels selected from FIG. 3E and indicated by asterisks on FIG. 3E are shown in FIGS. 3C and 3F. In FIGS. 3C and 3F the solid traces and closed circles indicate the reference interferometry data sets and the dashed traces and open circles indicate the interferometry data set with the sample in position.

Figure 4A:
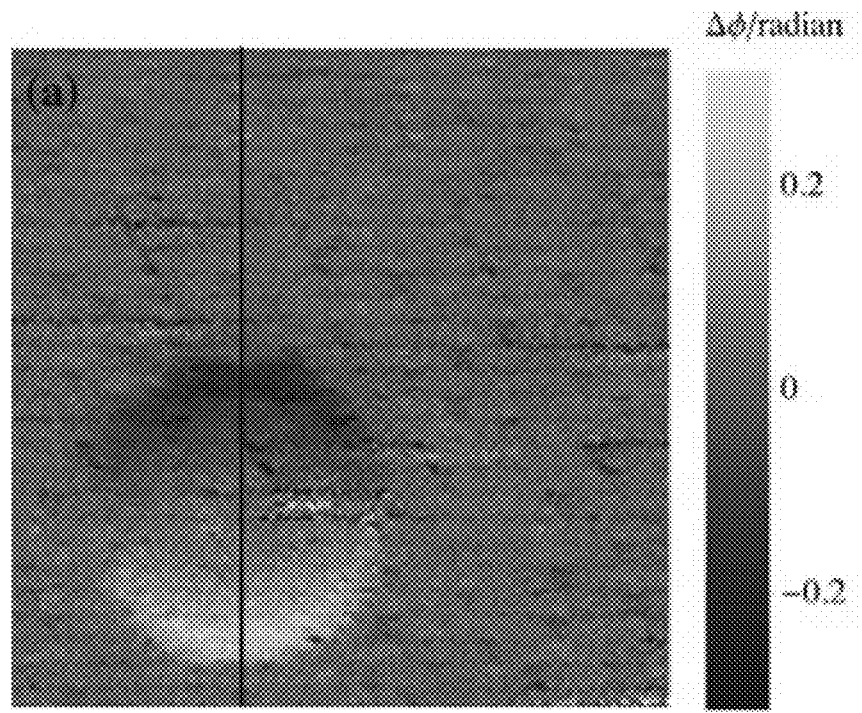
FIG. 4A shows $\Delta\varphi$/radian data experimental and analytical results from the method described in Example 1 and Example 2.
Figure 4B:
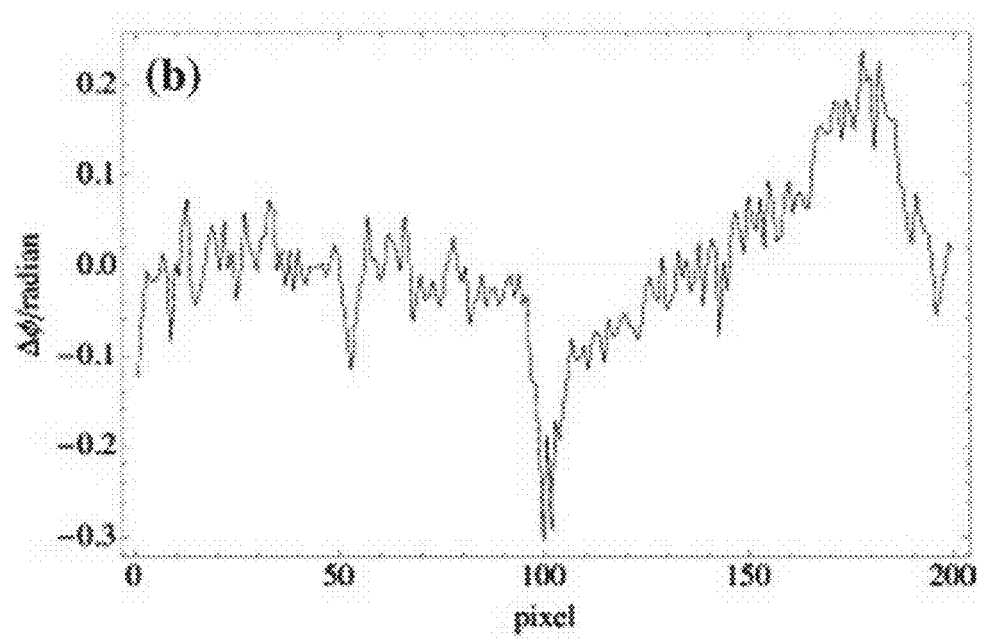
FIG. 4B shows $\Delta\varphi$/radian data experimental and analytical results from the method described in Example 1 and Example 2.
Figure 4C:
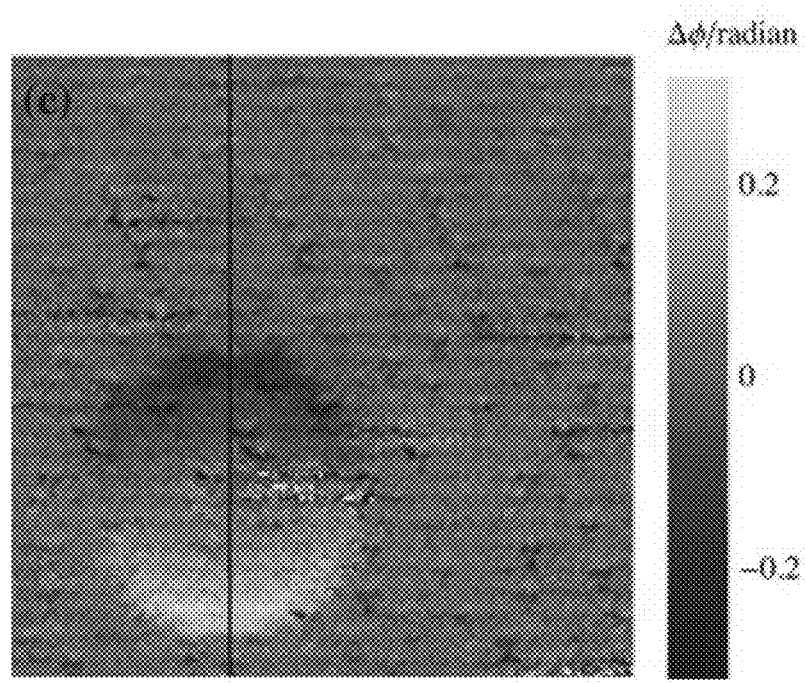
FIG. 4C shows $\Delta\varphi$/radian data experimental and analytical results from a discrete Fourier transform method.
Figure 4D:
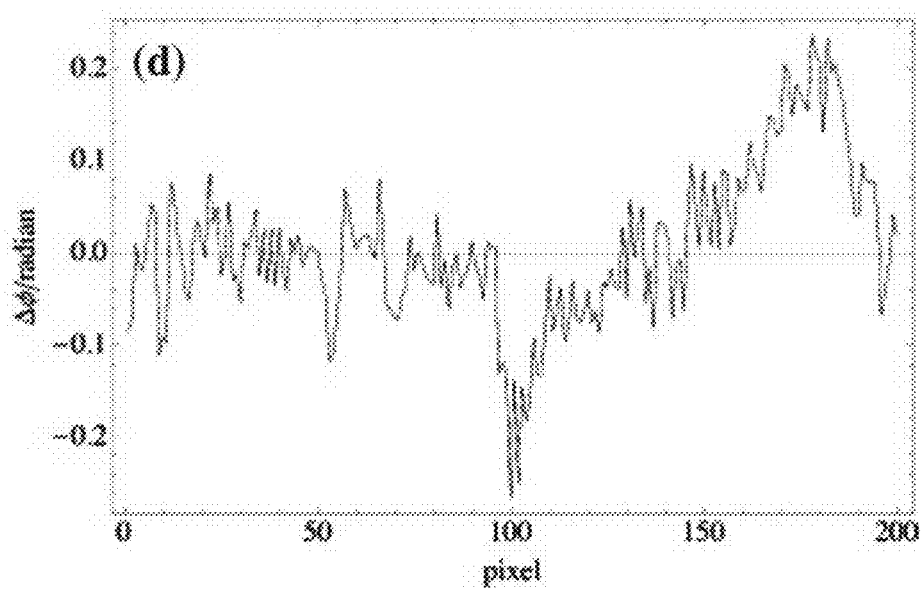
FIG. 4D shows $\Delta\varphi$/radian data experimental and analytical results from a discrete Fourier transform method.

FIGS. 4A-4D compare the method described in Example 1 and Example 2 with the discrete Fourier transform method with best possible sampling for this data set. FIGS. 4A and 4B show the experimental and analytical results from the method described in Example 1 and Example 2 with 16-grating steps (4/3-period). FIGS. 4C and 4D show the experimental and analytical results from the discrete Fourier transform with 10-grating steps (1-period). As can be seen from a comparison of FIGS. 4A and 4C image artifacts from the phase grating support structure and analyzer grating support structure are diminished with the method described in Example 1 and Example 2 and a larger grating step pattern.

In FIG. 4, the method with 16-grating steps (4/3-period) is compared to the discrete Fourier transform method with 10-grating steps (1 period). The additional data does yield an improved image. This suggests that a procedure exists for matching support structure design with a basis set, not necessarily sinusoidal, and corresponding grating step structure, not necessarily equally spaced.

Assessments were made of 2D images of polystyrene spheres supported on a Polyimide film and imaged at the m=1 (58 mm) fractional Talbot distance to evaluate the disclosed method. The 16 grating steps covered a 4/3-period of the analyzer structure. For comparison a discrete Fourier transform method was used with 10-grating steps of a full period. Both a Levenberg-Marquardt method and method described above were compared to the discrete Fourier transform method. Both a Levenberg-Marquardt method and method described above can use any or all of the grating steps. The gratings used were fabricated with support structures that leak into the differential phase contrast (DPC) image. The new method was tested with several different selections of grating steps to find an optimum pattern for image processing.

The computational time for Eq. (6) for the sample data set was about 1 s running on a common workstation computer. That computation time was about three orders of magnitude faster than fitting Eq. (1) with a Levenberg-Marquardt routine and about the same speed as calculating with the discrete Fourier transform method. The differential phase contrast image of one 50-µm-diameter sphere, depicted in FIG. 2A, is shown after baseline correction (the mean differential phase contrast of a 50×50 pixel region near the sphere) to remove the phase shift from the Polyimide film support. The sensitivity of the phase contrast experiment for light atom samples such as polystyrene when imaged at 25 keV is remarkable. The line probe through the sphere, depicted in FIG. 2B, shows the sphere edges and center. Two pixels along the line probe were selected for further examination; the pixel at {row=104,column=70}, FIG. 2C, represents a typical fit while the pixel at {96,70}, FIG. 2(f), has a large $\chi_v^2$ that may be attributed to the support structures in Phase grating 130 and Analyzer grating 150. The support structure was visually apparent in the differential phase image, FIG. 2A, as well as in the transmission and dark-field images (not shown).

As an illustration of the robustness and flexibility of the new method, the data from the 7th grating step was eliminated from the processing. For comparison, the discrete Fourier transform method is applied to the 10-grating step data set, also with omission of the 7th grating step. The results in FIG. 3 show a poor fit to the data points, more noise in the differential phase contrast image, and much higher $\chi_v^2$ values.

The results of several fitting methods and grating step selections are compared in FIG. 6 of the drawings. The Levenberg-Marquardt and new method are nearly equivalent for use with a full period of interferometry data or with under or oversampling. The discrete Fourier transform method performs worse than the other methods when used with a partial data set. The new method gives roughly equivalent results for grating step patterns of [1-10], [1-6, 8-10], and [2-11] for a single pixel as described in FIG. 6 and for differential phase contrast images (not shown). The [1-16] grating step pattern does yield a visually better image as will be discussed next. FIG. 6 compares the results of using the three methods to analyze pixel {104,70}.

Example 3

The second sample tested was a calcium-carbonate-rich shell of a foraminifera, a one-cell protist, which shows a highly structured, millimeter-sized prolate object in a tomographic study. The reconstructed absorption and differential phase images demonstrate the applicability of this new method.

Figure 5C:
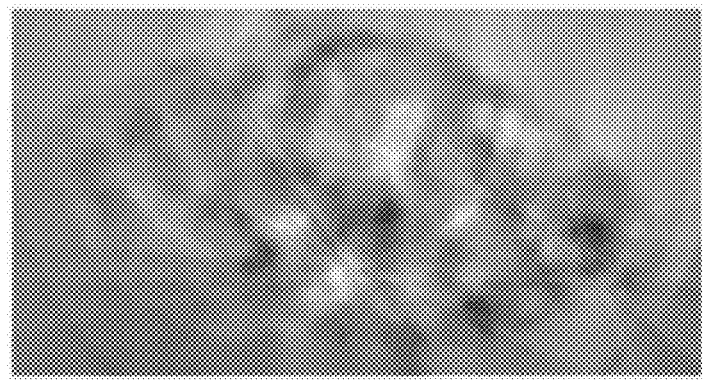
FIG. 5C shows a filtered back-projection reconstruction of the differential phase contrast images.
Figure 5B:
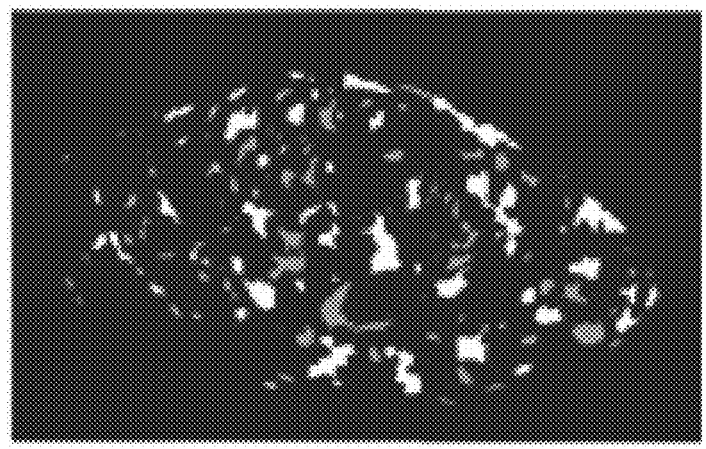
FIG. 5B shows an algebraic tomography reconstruction of the differential phase contrast images based on Eq. (10) followed by two-level segmentation to emphasize positive and negative regions of $\Delta\varphi$ values.
Figure 5A:
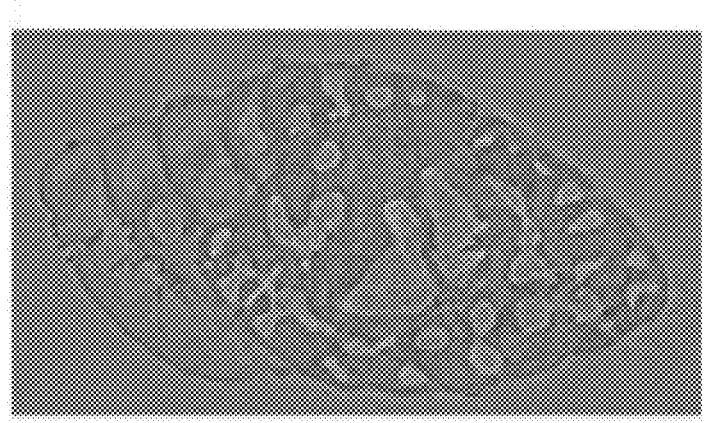
FIG. 5A shows a filtered back-projection reconstruction of a sinogram constructed from transmission images based on Eq. (9).

Images from FIGS. 5A-5C are slices from a tomographic volume. FIG. 5A shows a filtered back-projection reconstruction of a sinogram constructed from transmission images based on Eq. (9). FIG. 5B shows an algebraic tomography reconstruction of the differential phase contrast images based on Eq. (10) followed by two-level segmentation to emphasize positive and negative regions of $\Delta \varphi$ values. FIG. 5C shows a filtered back-projection reconstruction of the differential phase contrast images using the imaginary reconstruction kernel described by Pfeiffer and co-workers.

Uniformity may be seen in the X-ray transmission image in FIG. 5A. The differential phase contrast image shows a significantly different structure, especially when the differences are highlighted in a two-level segmentation as shown in FIG. 5B with white regions for positive $\varphi$ values and gray for negative $\varphi$ values. The differential phase contrast sinogram was reconstructed with algebraic reconstruction tomography. FIG. 5C shows an alternative reconstruction.

The methods and techniques described herein may provide a fast, robust, easily implemented, and flexible method compared to other previously known techiniques. These methods offer a route to tuning data acquisition so as to reduce the artifacts from phase and analyzer grating support structures.

Example 4

Gratings

A hardware solution for better clinical computed tomography (CT) imaging is described. X-ray optics (microfabricated absorption and phase contrast linear gratings for X-ray interferometry) may be used as part of a method to reduce X-ray dose to a patient and to increase image contrast. The present example describes fabrication techniques for X-ray optics to increase performance and further reduce X-ray dose.

Grating interferometers may be used expanding the field-of-view of the clinical computed tomography (CT) imaging, with larger gratings being used to further enhance the images.

X-ray optics for grating-based X-ray interferometry may be based on linear structures of X-ray absorbers or phase contrast materials deposited on thin silicon wafers. Such absorbers may have high-aspect ratio gold features with widths of 2 microns, heights of over 50 microns and a periodicity between features of 4 microns. At one point in the interferometer, an absorption grating is used to create phase coherence in the X-ray beam. The ray-tracing analysis used to in such configurations correctly notes the X-ray paths through the gold absorber and between adjacent gold absorbers, but fails to account for X-ray paths that interact with edges of the gold absorber. With all laboratory X-ray sources and most synchrotron sources, the non-parallel X-ray radiation will lead to appreciable X-ray flux encountering edges of the gold absorbers. Preliminary ray-tracing indicates these glancing interactions are leading to loss of phase contrast signal. Although it may be ideal to use of parallel X-ray radiation, doing so may not be practical for compact or room size imaging systems. Gradient-index (GRIN) optic technology may be applied to the sides of the microfabricated structures. For the X-ray energies used in medical imaging, elements from the first, second, and third rows of the transition metals can be used to fabricate a gradient-index along the sides of the X-ray optics. For example, the G0 absorption grating can be fabricated with gold as the main X-ray absorber, but then coated with silver, then copper so as to use GRIN technology to improve X-ray interferometry performance.

Illustration

Let us return to the development of Eqs. (5) to (7). First, let us simplify the discussion by considering a single pixel. Then, Eq. (5) reduces to the scalar D for the deviation, a data vector $\bar{c}$, and a fit vector $\bar{\hat{c}}$. The data and fit vectors have length M, the number of grating steps. The deviation may be defined as before:

$$D = \sum_{g=1}^{M} (c_g - \hat{c}_g)^2. \qquad (A1)$$

$\hat{c}_g$ may be expanded as $$\hat{c}_g = \sum_{\mu=1}^{3} B_{g\mu} a_\mu, \qquad (A2)$$

where B is an M×3 matrix of basis vectors spanning an M-dimensional vector space. Recall $\bar{\hat{c}}$ is a fit vector in the M-dimensional vector space with three degrees of freedom, given by the coefficients $\bar{a}$ and the basis vectors in B. It is desirable to minimize the distance, Eq. (A1), between the data vector $\bar{c}$ and the fit vector $\bar{\hat{c}}$. Using the calculus of variations, Eq. (A1) may be differentiated with respect to the three coefficients $a_v$ to get $$\frac{\partial D}{\partial a_v} = \sum_{g=1}^{M} 2(c_g - \hat{c}_g)^1 \frac{\partial \hat{c}_g}{\partial a_v}, \qquad (A3)$$

where $$\frac{\partial \hat{c}_g}{\partial a_v} = \sum_{\mu=1}^{3} B_{g\mu} \delta_{\mu v}, \qquad (A4)$$

and where $\delta_{\mu v}$ is the Dirac delta function. Substituting Eq. (A4) into Eq. (A3), gives an intermediate result:

$$\frac{\partial D}{\partial a_v} = \sum_{g=1}^{M} 2(c_g - \hat{c}_g)^1 \cdot B_{gv}. \qquad (A5)$$

Then, for $v=1 \ldots 3$, set $$\frac{\partial D}{\partial a_v} = 0$$

to seek the closest alignment of the fit vector $\bar{\hat{c}}$ with the data vector $\bar{c}$. Then, Eq. (A5) becomes $$0 = \sum_{g=1}^{M} c_g B_{gv} - \sum_{g=1}^{M} \hat{c}_g B_{gv}, \qquad (A6)$$

-continued $$0 = \sum_{g=1}^{M} c_g B_{gv} - \sum_{g=1}^{M} \left( \sum_{\mu=1}^{3} B_{g\mu} a_\mu \right) B_{gv}. \quad (A7)$$

Now, solving for $a_\mu$ (as $\bar{a}$) via a sequence of matrix multiplication, transpose, and inverse operations:

$$\sum_{g=1}^{M} \left( \sum_{\mu=1}^{3} B_{g\mu} a_\mu \right) B_{gv} = \sum_{g=1}^{M} c_g B_{gv}, \quad (A8)$$

$$\sum_{g=1}^{M} B_{vg}^T \left( \sum_{\mu=1}^{3} B_{g\mu} a_\mu \right) = \sum_{g=1}^{M} B_{vg}^T c_g, \quad (A9)$$

$$\sum_{\mu=1}^{3} \left( \sum_{g=1}^{M} B_{vg}^T B_{g\mu} \right) a_\mu = \sum_{g=1}^{M} B_{vg}^T c_g, \quad (A10)$$

$$\sum_{\mu=1}^{3} (B^T \cdot B)_{v\mu} a_\mu = (B^T \cdot \bar{c})_v, \quad (A11)$$

$$[(B^T \cdot B) \cdot \bar{a}]_v = (B^T \cdot \bar{c})_v, \quad (A12)$$

$$(B^T \cdot B) \cdot \bar{a} = B^T \cdot \bar{c}, \quad (A13)$$

$$\bar{a} = (B^T \cdot B)^{-1} \cdot B^T \cdot \bar{c}. \quad (A14)$$

Recall Eqs. (6) and (7) for all pixels:

$$\bar{a} = G \cdot \bar{c}, \quad (A15)$$

$$G = (B^T \cdot B)^{-1} \cdot B^T. \quad (A16)$$

The reduced chi-square statistic is the chi-square divided by the degrees of freedom:

$$\chi_v^2 = \frac{1}{v} \sum_{g=1}^{M} \frac{(c_g - \hat{c}_g)^2}{\sigma_g^2} \quad (A17)$$

$$= \frac{1}{(M-3-1)} \sum_{g=1}^{M} \frac{(c_g - \hat{c}_g)^2}{c_g}, \quad (A18)$$

where it was assumed that the standard deviations are given by the square root of the number of counts.

Further embodiments consistent with the descriptions herein may utilize a three-grating interferometer. Additionally, methods used herein may aid in the removal of image artifacts from grating support structures in the images resulting from those methods. For example, grating steps may either be skipped or spaced such that image artifacts are minimized.

Imaging techniques described herein may, for example, comprise providing a beam source; providing a beam detector; configuring the beam source and the beam detector such that a beam path connects the beam source and the beam detector; positioning an object in the beam path; positioning a phase grating in the beam path; positioning an analyzer grating in a first position in the beam path; projecting a first beam along the beam path thereby producing a first data set; moving the analyzer grating from the first position to a second position; projecting a second beam along the beam path thereby producing a second data set; moving the analyzer grating from the second position to a third position; projecting a third beam along the beam path thereby producing a third data set; conducting a regression analysis fitting pixel data from a group of data sets comprising the first data set, the second data set and the third data set to a predetermined function to establish a set of fitting coefficients; wherein the fitting coefficients characterize a set of interference properties associated with the object; wherein the predetermined function is dependent on the analyzer grating position; and wherein the predetermined function contains sinusoidal functions. In a related example, the imaging techniques may further comprise preparing a differential phase contrast image based on a set of results from the regression analysis. In another related example, the first beam may have a spatially-periodic intensity at the beam detector. In another related example, the object is a nonliving object. In another related example, the object may comprise human tissue. In another related example, the phase grating may comprise planar structures oriented parallel to the beam path. In another related example, the phase grating may be a spatially periodic array of beam transmitting apertures. In another related example, the first beam may be a neutron beam. In another related example, the first beam may be an x-ray beam. In another related example, the first beam may be a substantially monochromatic beam. In another related example, the predetermined function may contain sine and cosine terms. In another related example, the regression analysis may occur on a pixel by pixel basis. In another related example, the analyzer grating may be a periodic structure. In another related example, the phase grating may be a periodic structure. In another related example, the first beam may sequentially pass through the object, then through the phase grating and then through the analyzer grating. In another related example, the phase grating may be constructed of a material that absorbs the beam. In another related example, the fitting of pixel data may occur based on the relationship expressed in the equation:

$$\hat{c}_{gp} = \sum_{\mu=1}^{n} B_{g\mu} a_{\mu p}$$

wherein $\hat{c}_{gp}$ is an expected exposure based on grating position; wherein B is a fitting function matrix that is a M×n matrix wherein M is a number of exposure steps and g is an exposure step number; wherein a is a matrix containing the set of fitting coefficients and wherein n is an integer that is at least 3. In another related example, the fitting of pixel data may occur based on the relationship expressed in the equations:

$$a = G \cdot c$$

and $$G = (B^T \cdot B)^{-1} \cdot B^T$$

wherein a is a matrix containing the set of fitting coefficients; wherein B is a fitting function matrix that is a M×n matrix; wherein c is a M×N matrix wherein M is a number of exposure steps and wherein N is a number of pixels in a captured image from the first data set and wherein n is an integer that is at least 3. In another related example, a first grating step distance representing the distance between the first position and the second position may be different than a second grating step distance representing the distance between the second position and the third position. In another related example, the analyzer grating may have an analyzer grating period and a first grating step distance representing the distance between the first position and the second position that is less than the analyzer grating period.

The above-described embodiments have a number of independently useful individual features that have particular utility when used in combination with one another including combinations of features from embodiments described separately. There are, of course, other alternate embodiments which are obvious from the foregoing descriptions of the invention, which are intended to be included within the scope of the invention, as defined by the following claims.

What is claimed is:

1. An imaging technique comprising:
   a) providing a beam source;
   b) providing a beam detector;
   c) configuring the beam source and the beam detector such that a beam path connects the beam source and the beam detector;
   d) positioning an object in the beam path;
   e) positioning a phase grating in the beam path;
   f) positioning an analyzer grating in a first position in the beam path;
   g) projecting a first beam along the beam path thereby producing a first data set;
   h) moving the analyzer grating from the first position to a second position;
   i) projecting a second beam along the beam path thereby producing a second data set;
   j) moving the analyzer grating from the second position to a third position;
   k) projecting a third beam along the beam path thereby producing a third data set;
   l) conducting a regression analysis fitting pixel data from a group of data sets comprising the first data set, the second data set and the third data set to a predetermined function to establish a set of fitting coefficients;
   m) wherein the set of fitting coefficients characterize a set of interference properties associated with the object;
   n) wherein the predetermined function is dependent on the analyzer grating position; and
   o) wherein the predetermined function contains sinusoidal functions;
   p) wherein the fitting of pixel data occurs based on the relationship expressed in the equation:

$$\hat{c}_{gp} = \sum_{\mu=1}^{n} B_{gp} a_{\mu p}$$

q) wherein $c_{rjv}$ is an expected exposure based on grating position;
   r) wherein B is a fitting function matrix that is a M×n matrix wherein M is a number of exposure steps and g is an exposure step number;
   s) wherein a is a matrix containing the set of fitting coefficients;
   t) wherein n is an integer that is at least 3 and
   u) wherein y is a pixel number.

2. The imaging technique of claim 1 further comprising preparing a differential phase contrast image based on a set of results from the regression analysis.

3. The imaging technique of claim 1 wherein the first beam has a spatially-periodic intensity at the beam detector.

4. The imaging technique of claim 1 wherein the object comprises human tissue.

5. The imaging technique of claim 1 wherein the predetermined function has a set of basis vectors.

6. The imaging technique of claim 1 wherein the phase grating is a spatially periodic array of beam transmitting apertures and wherein the phase grating comprises planar structures oriented parallel to the beam path.

7. The imaging technique of claim 1 wherein the first beam is a neutron beam.

8. The imaging technique of claim 1 wherein the first beam is an x-ray beam.

9. The imaging technique of claim 1 wherein the predetermined function contains sine and cosine terms.

10. The imaging technique of claim 1 wherein the regression analysis occurs on a pixel by pixel basis.

11. The imaging technique of claim 1 wherein the analyzer grating is a periodic structure.

12. The imaging technique of claim 1 wherein the phase grating is a periodic structure.

13. The imaging technique of claim 1 wherein the first beam sequentially passes through the object, then through the phase grating and then through the analyzer grating.

14. The imaging technique of claim 1 wherein the phase grating is constructed of a material that absorbs the beam.

15. The imaging technique of claim 1 wherein a first grating step distance representing the distance between the first position and the second position is different than a second grating step distance representing the distance between the second position and the third position.

16. The imaging technique of claim 1 wherein the analyzer grating has an analyzer grating period and a first grating step distance representing the distance between the first position and the second position that is less than the analyzer grating period.

17. An imaging technique comprising:
   a) providing a beam source;
   b) providing a beam detector;
   c) configuring the beam source and the beam detector such that a beam path connects the beam source and the beam detector;
   d) positioning an object in the beam path;
   e) positioning a phase grating in the beam path;
   f) positioning an analyzer grating in a first position in the beam path;
   g) projecting a first beam along the beam path thereby producing a first data set;
   h) moving the analyzer grating from the first position to a second position;
   i) projecting a second beam along the beam path thereby producing a second data set;
   j) moving the analyzer grating from the second position to a third position;
   k) projecting a third beam along the beam path thereby producing a third data set;
   l) conducting a regression analysis fitting pixel data from a group of data sets comprising the first data set, the second data set and the third data set to a predetermined function to establish a set of fitting coefficients;
   m) wherein the set of fitting coefficients characterize a set of interference properties associated with the object;
   n) wherein the predetermined function is dependent on the analyzer grating position;

o) wherein the fitting of pixel data occurs based on the relationship expressed in the equations:

$a = G*C$ and $G = (B^T \cdot B)^{-1} \blacksquare B^T$;

p) wherein a is a matrix containing the set of fitting coefficients;
q) wherein B is a fitting function matrix that is a M×n matrix;
r) wherein c is a M×N matrix wherein M is a number of exposure steps and wherein N is a number of pixels in a captured image from the first data set;
s) wherein n is an integer that is at least 3;
t) wherein G is a fitted M×N matrix and
u) wherein superscript T indicates the matrix transpose.

18. The imaging technique of claim 17 further comprising preparing a differential phase contrast image based on a set of results from the regression analysis.

19. The imaging technique of claim 17 wherein the predetermined function contains sinusoidal functions.

20. The imaging technique of claim 17 wherein the predetermined function has a set of basis vectors.

* * * * *

UNITED STATES PATENT AND TRADEMARK OFFICE
CERTIFICATE OF CORRECTION

PATENT NO. : 10,117,629 B2  
APPLICATION NO. : 14/958882  
DATED : November 6, 2018  
INVENTOR(S) : Leslie G. Butler, Kyungmin Ham and Warren W. Johnson Page 1 of 1

It is certified that error appears in the above-identified patent and that said Letters Patent is hereby corrected as shown below:

In the Claims

In Column 11 in Claim 1 the lines reading:
"p) wherein the fitting of pixel data occurs based on the relationship expressed in the equation:

$$\hat{c}_{gp} = \sum_{\mu=1}^{n} B_{gp} a_{\mu p}$$

q) wherein $c_{rjv}$ is an expected exposure based on grating position;"

Should read as follows:
--- p) wherein the fitting of pixel data occurs based on the relationship expressed in the equation:

$$\hat{c}_{gp} \sum_{\mu=1}^{n} B_{g\mu} a_{\mu p} \; ;$$

q) wherein $\hat{c}_{gp}$ is an expected exposure based on grating position; ---

In Column 13 in Claim 17 the line reading:
" $a = G*C$ and $G = (B^r \cdot B)^{-1} \blacksquare B^r$ ; "

Should read as follows:
--- $\mathbf{a} = \mathbf{G} \cdot \mathbf{c}$ and $\mathbf{G} = (\mathbf{B}^T \cdot \mathbf{B})^{-1} \cdot \mathbf{B}^T$ ; ---

Signed and Sealed this  
Twelfth Day of March, 2019

Andrei Iancu  
*Director of the United States Patent and Trademark Office*